US005645709A

United States Patent [19]
Birch et al.

[11] Patent Number: 5,645,709
[45] Date of Patent: Jul. 8, 1997

[54] METHODS AND APPARATUS FOR ELECTROCHEMICAL MEASUREMENTS

[75] Inventors: Brian Jeffrey Birch, Chelveston; Nicholas Andrew Morris, Kempston, both of England; Vincent Bonnafoux, Meyreuil, France

[73] Assignee: Van den Bergh Foods Co., Division of Conopco, Inc., Ill.

[21] Appl. No.: 350,862

[22] Filed: Dec. 7, 1994

[30] Foreign Application Priority Data

Dec. 8, 1993 [GB] United Kingdom ............ 9325189

[51] Int. Cl.$^6$ ................................ G01N 27/26
[52] U.S. Cl. ............... 205/775; 205/697; 422/69; 422/82.01
[58] Field of Search ........... 204/153.12, 153.1, 204/403, 412, 138; 435/288, 291, 817; 436/95; 422/69

[56] References Cited

U.S. PATENT DOCUMENTS

| | | | |
|---|---|---|---|
| 4,127,448 | 11/1978 | Schick et al. | 204/412 |
| 4,929,545 | 5/1990 | Freitas | 435/14 |
| 5,120,420 | 6/1992 | Nankai et al. | 204/153.12 |
| 5,192,415 | 3/1993 | Yoshioka et al. | 204/153.12 |

FOREIGN PATENT DOCUMENTS

| | | |
|---|---|---|
| 170375 | 2/1986 | European Pat. Off. . |
| 186 386 | 7/1986 | European Pat. Off. . |
| 255291 | 2/1988 | European Pat. Off. . |
| 275 924 | 2/1990 | German Dem. Rep. . |
| 1 533 194 | 11/1978 | United Kingdom . |
| 2 154 003 | 8/1985 | United Kingdom . |
| 2 202637 | 9/1988 | United Kingdom . |
| 81/03546 A1 | 12/1981 | WIPO . |
| 89/01047 | 2/1989 | WIPO . |

OTHER PUBLICATIONS

Partial European Search Report for EP 91301661 No month or year available.
Search Report for GB 9220701.8 No month or year available.
Chemical Abstracts, vol. 107, No. 16, 19 Oct. 1987, M. Hangos Mahr et al.: "Determination of reducing sugars using a flow–type automatic analyzer", p. 825, right–hand column; Ref. No. 146571m.
Analytical Abstracts Database, Royal Society of Cambridge, GB; H. Ohura et al.; "Potentionmetric flow–injection analysis of glucose using hexacyanoferrate (III)–hexacyanoferrate (II) potential buffer" accession No. 50–09–D–00093 & Anal. Sci., vol. 3, No. 5, 453–456, 1987 No month available.
Sensors and Actuators, vol. 15 (1988), pp. 199–207 Micro–Biosensors for Clinical Analyses, Tamiya & Karueb No month available.
International Search Report No month or year available.

Primary Examiner—Bruce F. Bell
Attorney, Agent, or Firm—Gerard J. McGowan, Jr.

[57] ABSTRACT

A method for the electrochemical determination of the reducing sugars content of an aqueous solution in a thin layer electrochemical measuring device, preferably a capillary fill device, wherein an inner surface of the device is coated with a soluble redox mediator, the device including means for producing an alkaline environment within the device. In a preferred method the redox mediator comprises potassium ferricyanide providing ferricyanide ions in saturated solution and lithium hydroxide providing hydroxide ions in an excess amount of from 1 to 3 molar. The invention also provides a capillary fill device having a guard electrode between the reference and working electrodes.

17 Claims, 14 Drawing Sheets

METHODS AND APPARATUS FOR ELECTROCHEMICAL MEASUREMENTS

FIELD OF THE INVENTION

This invention relates to methods and apparatus for making electrochemical measurements and in one aspect concerns electrochemical determination of the reducing sugar content of aqueous solutions, with special but not exclusive application to determination of the reducing sugar content of farm silage liquors.

BACKGROUND TO THE INVENTION

It is well known that silage has to be treated and stored under special conditions in order, as far as possible, to maintain its nutritional content for winter feeding. During storage, a number of chemical changes take place, and it can be important to know a number of nutritional parameters of the silage, for example to facilitate determination of when the silage is ready to be used. One of the most important parameters is the reducing sugar content. Also, generally in the production of food and drink for human and animal consumption and with other biological liquids, there are many instances when it would be valuable to be able to assess readily the reducing sugar content.

Reverting to silage, there is already known an analysing system which is able to determine various nutritional parameters of a liquor obtained by squeezing a silage sample, including the free sugar content. However, this system is relatively expensive and complex, and depends on wet chemistry. Such a system is described in GB 2202637A.

In the field of biosensors, there is known from EP 0170375A a capillary-fill device (CFD). In a common form, this comprises two plates separated by a gap sufficiently small that liquid can be drawn into it by capillary action. The internal faces of the plates carry printed electrodes, and may also carry a reagent layer deposited, e.g. by screen printing. This reagent layer is selected with due regard to the liquid to be drawn in, to carry out a particular test. EP 0255291A discloses a CFD including an oxidase enzyme specific for a particular sugar to be detected, e.g. glucose oxidase for determination of the concentration of glucose in a liquid, for example a blood sample. This device is thus specific to a particular sugar so that only one particular sugar can be tested at a time.

It is also known to determine the sugars content of a solution by making use of the reducing properties of sugars, for example involving reduction of ferricyanide ion to ferrocyanide ion. The resulting ferrocyanide ion is then detected by a convenient method, for example spectrophotometrically, or possibly electrochemically, although spectrophotometric methods have generally been preferred (e.g. by measuring the decrease in yellow colour of a solution, when the ferrocyanide ion system is used). Traditionally this has been done at an alkaline pH, for example at pH 9–12, in a hot solution in the presence of a catalyst (e.g. $Ni^{2+}$, $Co^{2+}$). Such a technique usually takes around thirty minutes to provide a result to the user.

The quantitative determination of sugars by making use of their reduction properties has also been done at acidic pH's; however, in this case the products detected are produced by a different pathway, in which the sugar hydrolyses. The total reducing sugars determination is made by measuring the resulting concentration of the reduced form of the reactant compound, for example the ferrocyanide ion concentration, usually by spectrophotometric methods, or occasionally potentiometrically.

The determination of the reducing sugars content of a solution using conventional spectophotometric techniques has required the facilities and trained personnel of a laboratory. Also, the methods and techniques traditionally used for the determination of the total sugars content of solutions have often been time consuming and laborious.

Another known technique of sugars determination is pulsed amperometric detection, e.g. as described in "Triple-Pulse Amperometric detection of Carbohydrates after Chromatographic separation", Hughes and Johnson, Analytica Chimica Acta, 149 (1983), 1–10. This technique involves oxidising the sugar in a sample directly at a working electrode. This technique is most generally applicable for the determination of single sugars (such as for example are analyzed for when eluting a sample from a chromatographic column), and is only applicable to relatively small amounts of sugar (of the order of nanomoles). This technique also has the disadvantage that it requires the application of several different potentials to the test device, thereby requiring that the method be carried out in several different steps. The method is also only suitable to be carried out in an analytical laboratory, and requires the use of expensive equipment and skilled operators.

Not only for testing silage liquors, but for testing various aqueous liquids related to food and drink production, it would be highly advantageous to provide a simple method and device for measuring on site the sugar content of an aqueous liquid, not dependent on the presence in the liquid of any one particular sugar, and more especially with the aim of measuring the total reducing sugar content of the liquid.

SUMMARY OF THE INVENTION

According to one aspect of the invention, therefore, there is provided a method of determining the content of reducing sugar in an aqueous solution, comprising forming a thin layer of a solution to be tested in an alkaline environment and in the presence of a soluble redox mediator; and determining electrochemically the amount of reduction product of the redox mediator.

It is to be noted that the redox mediator is not specific to any particular sugar and that the reaction which takes place in the device is non-enzymatic. However, in the presence of a redox agent, an alkaline environment is necessary to avoid sugar hydrolysis. This may be achieved for example by inclusion in the mediator of soluble alkaline producing substance, e.g. a soluble hydroxide. Alternatively, an alkaline environment may be generated in situ by the technique disclosed in WO94/15207.

The method is conveniently carried out in a thin layer electrochemical measurement device, such as a CFD, an inner surface of which includes a coating of at least one soluble redox mediator, possibly including a soluble alkaline producing substance such as an alkali metal hydroxide.

With a thin layer electrochemical measurement device, measurement can be carried out potentiometrically or coulometrically and either measurement technique can be used in practice of the present invention. Both techniques are well known in the field of electrochemical biosensors, and will not at this point be described in detail. However, the potentiometric measurement technique measures the changing potential at a working electrode with respect to a reference electrode; the coulometric technique measures the charge or current passing at a working electrode.

Whichever measurement technique is employed, it has been found that the accuracy of measurement can be adversely affected by diffusion of ions towards the working electrode. The accuracy of measurement depends on counting the ions produced in the volume of liquid adjacent the working electrode. Effectively, the reduced ions are re-oxidised at the working electrode and the totality of the electrons thus released is representative of the required measurement. If reduced ions from outside the volume in question diffuse into the volume and are incorporated into the measurement, the measurement is falsified.

According to another aspect of the invention, therefore, there is provided an electrochemical measuring device having a working electrode and a reference electrode on an internal fluid-receiving surface, wherein the working electrode and the reference electrode have between them a guard electrode maintained substantially at the same potential as the working electrode.

In use, the guard electrode acts to prevent diffusion of reduced ions into the volume of liquid adjacent the working electrode on which measurement depends. Thus, in the case where, in accordance with the first aspect of the invention, the reduced ions of the redox couple of a redox mediator tend to migrate towards the working electrode, these ions are oxidised when reaching the guard electrode, which is connected in a different circuit from the working electrode, and are therefore prevented from erroneously adding to the measured voltage or current. However, it should be made clear that the guard electrode according to the second aspect of the invention, while being especially useful in the method according to the first aspect of the invention, is not limited to use in this method, and can find application in thin layer electrochemical measurement devices used in other methods and applications.

The first aspect of the invention is specifically concerned with measurement of reducing sugars content in an aqueous liquid such as silage liquors, e.g. using a thin layer electrochemical sensor. A preferred thin layer electrochemical sensor is a capillary fill device (CFD).

CFD's comprise two plates, e.g. of ceramic, glass, or plastics material, spaced with a small gap. On the inside surface of the one plate is deposited a reference electrode, and spaced from it on the surface of the plate is a working electrode. The working electrode is maintained at a relatively high potential. On the inside surface of the other plate may be screen printed a reagent layer appropriate to the substance to be tested in a liquid sample. Contact pads e.g. of carbon on the electrodes enable measurement probes connected in an electrical measurement circuit to detect voltage or current at the working electrode with respect to the reference electrode, when the device is in use. CFD's of this form are in themselves known, e.g. as disclosed in EP 170375 A, and have been used for a variety of purposes, for example to measure pH values, to measure the glucose content in blood and plasma samples, to measure lactic acid concentration and to measure phosphate or nitrate concentrations. In the measurement of glucose content in a blood sample, the chemistry relied upon is the reaction of glucose with ferricyanide present in large excess, catalysed by glucose oxidase. The ferrocyanide produced by the reaction is measured by monitoring current flow between the counter and working electrodes.

In all the above instances, however, the detection carried out is of a single species in a relatively simple sample, using a reagent, commonly an enzyme, specific to the species to be detected.

In contrast, the present invention proposes use of a reagent in the form of a redox mediator in an alkaline environment, with the aim of measuring the total reducing sugar content in an aqueous solution which can contain a plurality of sugars. For example silage liquor, whilst commonly containing a predominance of glucose and fructose, may also contain other sugars such xylose and arabinose.

The redox mediator employed in the present invention requires to satisfy a number of criteria, most of which are generally well known from previous usage of redox mediators in enzymatic systems. In the case of a CFD, and for practising the present invention, it is amongst other criteria necessary for the redox mediator to be rapidly soluble, to react quickly with the analyte, and to produce a redox couple which has rapid and reversible electrochemistry with a working electrode suitable for practical use in the CFD. While a redox mediator such as ruthenium hexamine is a possibility, the ferricyanide ion is less expensive and has proven use in the CFD for testing blood samples.

In a preferred practice of the present invention, therefore, the redox agent is the ferricyanide ion, preferably present in an amount to form a substantially saturated solution (about 1 molar) when dissolved, whilst a preferred alkaline producing substance is lithium hydroxide, used at a concentration of between 1 and 3 moles and preferably about 2.5 moles, although any other alkali metal hydroxide such as sodium hydroxide is also usable. An appropriate binder may be incorporated with the redox agent and alkaline producing substance, if appropriate.

At this point it should be made clear that it is known, on a beaker scale, to measure the sugars content of an aqueous solution making use of a redox reaction having ferricyanide ions and sodium hydroxide as reagents. However, the necessary reaction has to be promoted at elevated temperature, typically around 80 degrees C., and even then the measurement takes some 30 minutes to carry out. Analysis is achieved by detecting the amount of ferrocyanide produced. This is usually done by a spectrophotometry technique.

Remarkably, however, in the present invention, the method can be practised in a CFD at room temperature, and the measurement generally completed within about 1 minute, and invariably less than 2 minutes.

The normal reaction which takes place is the catalytic oxidation of fructose, for example, with ferricyanide, and under alkaline conditions, is:

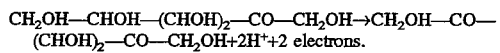

$$CH_2OH—CHOH—(CHOH)_2—CO—CH_2OH \rightarrow CH_2OH—CO—(CHOH)_2—CO—CH_2OH + 2H^+ + 2\text{ electrons.}$$

Although the mechanism by which it happens is not fully understood, as in the method of the present invention employing a thin layer electrochemical sensor, the required reaction not only takes place very quickly at room temperature, but far more electrons are released than expected. It appears possible that, in the confined space of a CFD, the large excess or high concentration of ferricyanide ions and alkali together with the rapid kinetics of a thin layer sample, are responsible for the enhanced reaction which takes place. Experiments appear to show that the rate of reaction slows appreciably when a high concentration of sugars is present, and thus relatively a lower concentration of ferricyanide and hydroxide ions. The method therefore appears to be most suitable for solutions containing sugars in concentrations of 0 to 25 mM. Concentrations of this level are typically to be found in silage liquors and many other biological liquids.

An additional and unexpected advantage of the method of the invention is that it is possible to "tune" the sensitivity of this electrochemical reaction for the quantitative determination of reducing sugars, depending on the concentration of reducing sugars in the sample to be tested. For example, if a relatively large amount of reducing sugar is present in the solution being tested, the determination can be carried out at a relatively low alkaline producing substance concentration. With sufficiently high concentrations of reducing sugars in the sample, it is even possible that the concentration of alkaline producing substance utilised in the thin layer measuring device may be less than 1 molar. Conversely, if a relatively low amount of reducing sugar is thought to be present in the sample, then the determination can be carried out at a relatively high alkaline producing substance concentration (e.g. 4–5 molar), thereby producing a relatively large current for a given amount of reducing sugar in the sample. Hence, in the measurement of a relatively large amount of sugar, the electrically measured value need not go "off the scale"; instead, the determination can be carried out at a lower concentration of alkaline producing substance. Thus an advantage of the invention is that it can be used to analyse samples which contain a broader range of reducing sugar concentrations than was previously possible.

A further advantage of the method is that it can be used to determine the total sugars of an aqueous solution, if the test solution is treated by a known method to convert the non-reducing sugars in the sample into reducing sugars. Conveniently this conversion may be carried out as a pre-treatment. A suitable pre-treatment may comprise, for example, the conversion of non-reducing sugars into reducing sugars using suitable enzymes. Such techniques will be readily understood by those skilled in the art.

The amount of reducing sugars in the sample can then be determined as described above.

Although the thickness of the thin layer of fluid sample in the device is not critical, it also appears that the above-described reaction is enhanced when the spacing between the plates of the CFD is less than 1 mm, preferably less than 0.5 mm, and most preferably in the range 0.1 to 0.2 mm. It appears likely that the kinetics of the reactive system, which are in any event rapid in a CFD, are still further improved when the thickness of the fluid layer is reduced.

The choice of electrode materials in the thin layer electrochemical device is also of some importance. A prime requirement for the reference electrode is that it shall be as insensitive as possible to the analyte. In the present invention, the reference electrode is preferentially of silver/silver chloride. On the other hand, the working electrode must be highly responsive to the analyte in order to restore the redox couple. In the present invention, a carbon or gold reference electrode is preferably employed, most preferably gold. When a guard electrode is employed, it is preferably of the same material as the working electrode.

The above-described CFD has been used successfully to practice the method of the invention for a number of aqueous solutions containing reducing sugars. However, it has been found that the response of the device to different types of sugar is subject to some variation when accurate quantitative assessment is required. Although responsive to both mono-saccharides and di-saccharides, the responses for some sugars such as sucrose are quantitatively less than for other reducing sugars such as glucose and fructose. Nevertheless, for many aqueous sugar-containing solutions, for example silage liquors, where glucose and fructose are dominant, the method gives accurate results, and for the first time provides a CFD, which can be disposable, which measures total reducing sugar content in a short time at room temperature, making it suitable for use on site, for example on site on a farm. Furthermore, it is believed that further development to enhance the sensor activity will result in a method and device fully capable of measuring the total reducing sugar content in aqueous solutions arising in many other fields.

For example, a further envisaged application is in determination of ripeness of vegetables and fruit. This would involve measuring the reducing sugars content of liquor expressed from a fruit or vegetable sample.

BRIEF DESCRIPTION OF THE DRAWINGS

Further features of the invention will be apparent from the following description of a practical method and device, given by way of example only. In the accompanying drawings.

DETAILED DESCRIPTION OF THE DRAWINGS

Figures 1A, 1B:
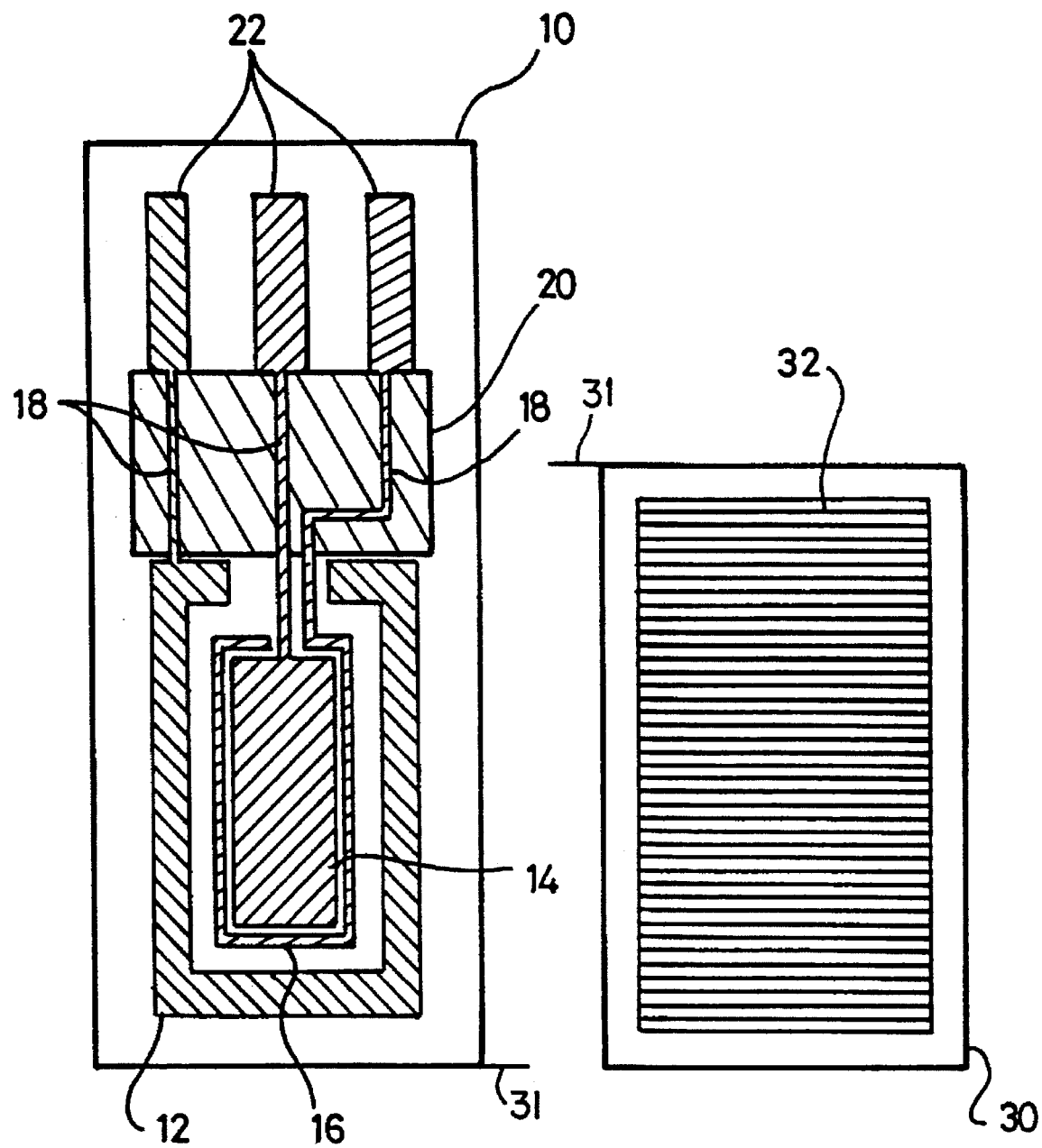
FIG. 1 is an explanatory view of a capillary fill device (CFD) designed for coulometric measurement; With FIG. 1a showing a bottom plate and FIG. 1b showing a top plate.

A capillary fill device (CFD) comprises two plates spaced by a small gap, say about 0.2 mm, whereby a liquid sample can be drawn into the space between the plates by capillary action. As shown in FIG. 1a, one plate 10, 10 mm×20 mm, made of a ceramic material, has deposited on it an electrode arrangement suited to the method of measurement, in this case coulometric. The first, outer electrode 12 is a reference electrode of silver/silver chloride, the second, inner electrode 14 is a working electrode of gold (although carbon could alternatively be used), and the third, intermediate electrode 16 is a guard electrode preferably of the same material as the working electrode. The electrodes are all 8 μm thick and are deposited using conventional screen printing techniques. Electrodes 14 and 16 are separated by a gap at about 150 μm. Conductors 18 extending through a dielectric layer 20 connect the electrodes to respective contact or terminal pads 22. Probes forming part of an electric measurement circuit shown in FIG. 2 are thus able to detect charge or current passing at the working electrode 14.

Figure 2:
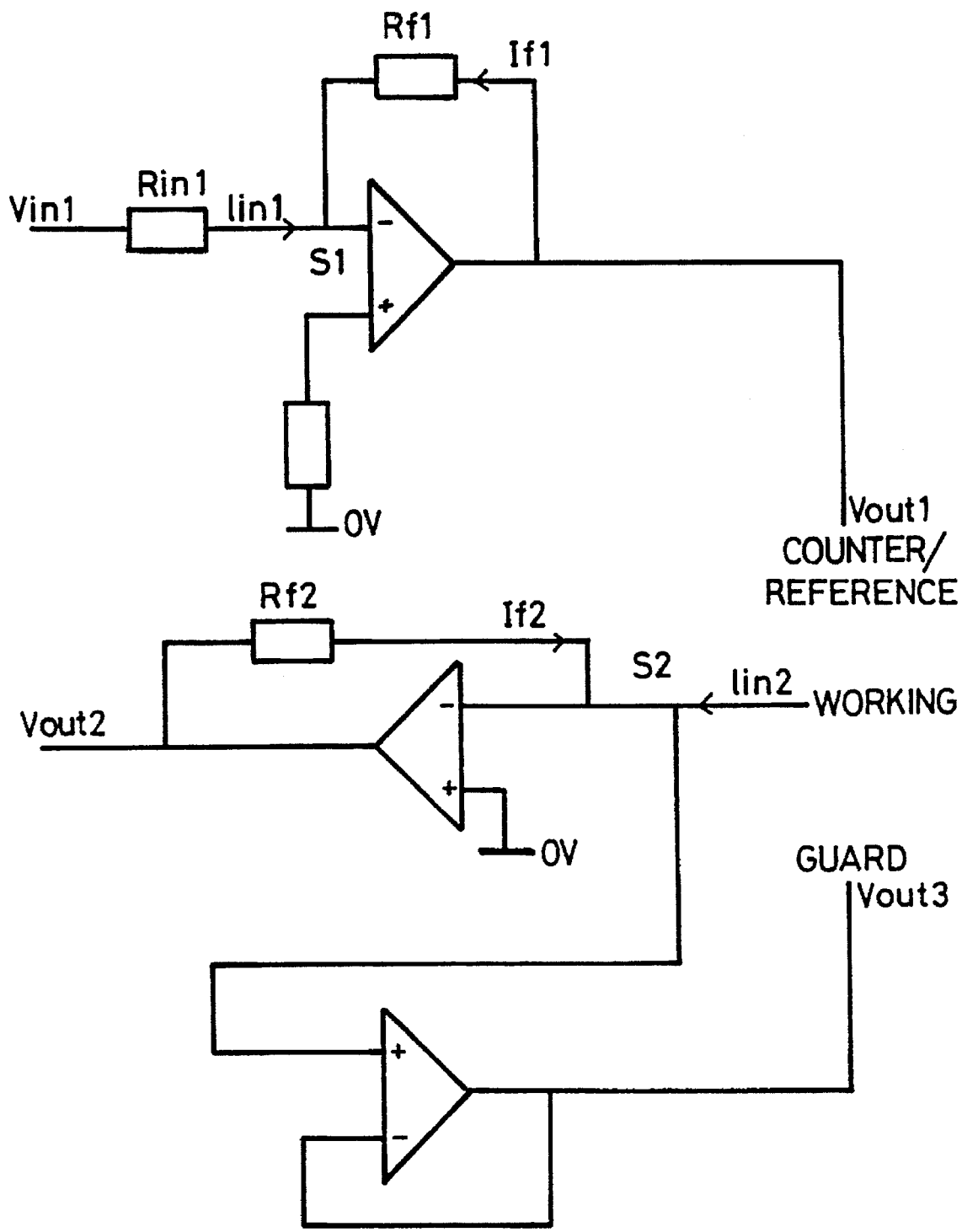
FIG. 2 is a measurement circuit for a coulometric CFD.

The coulometric measurement circuit shown in FIG. 2 is considered self-explanatory and will not be described in detail. Briefly, it establishes and maintains a stable reference potential at the reference electrode; collects current flowing through the working electrode and converts it into an analogue measurement signal; and maintains the guard electrode at the same potential as the working electrode whilst preventing any leakage of current from the guard electrode into the measurement signal. The final measurement signal is received by an A/D converter which feeds digital information to a processor controlled by software to compute the total current flowing at the working electrode over a given period of time. The result can be displayed on an LCD.

Figures 3A, 3B:
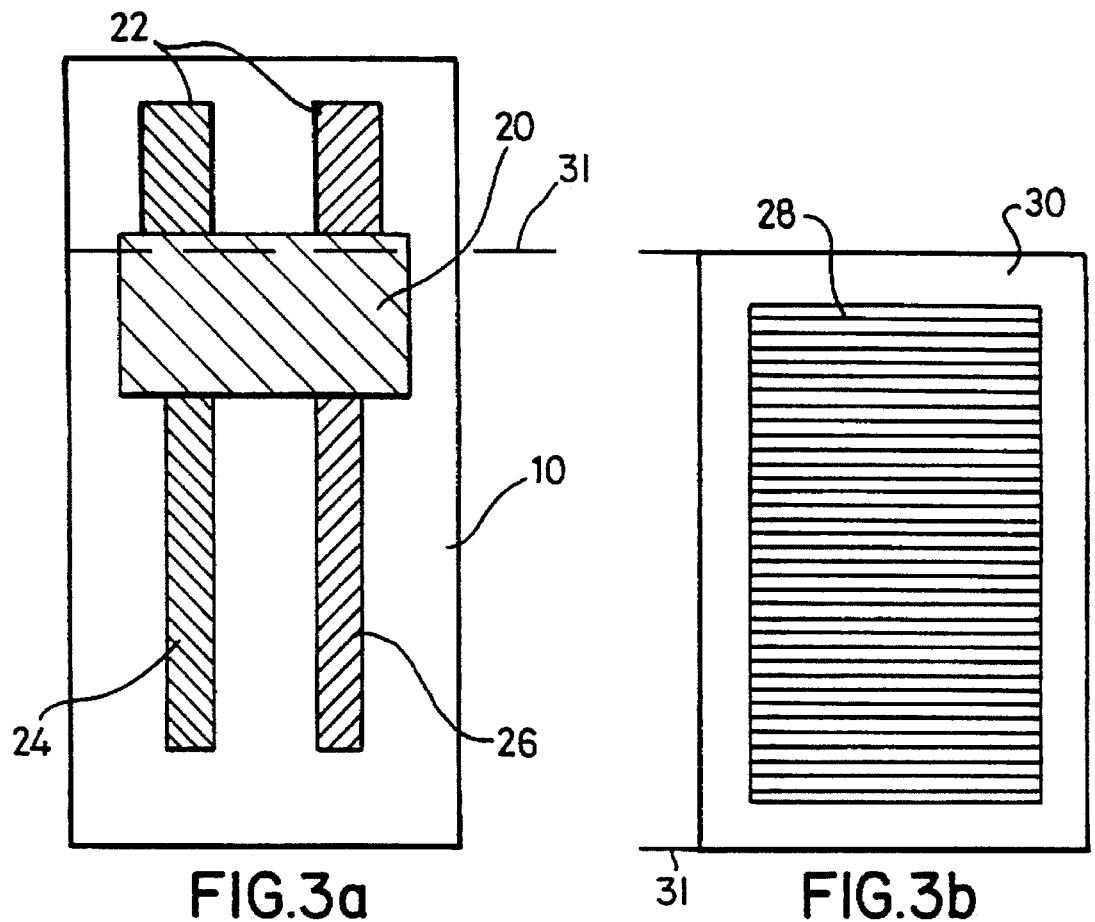
FIG. 3 is an explanatory view of a CFD designed for potentiometric measurement; With FIG. 3a showing a bottom plate and FIG. 3b showing a top plate.
Figure 4:
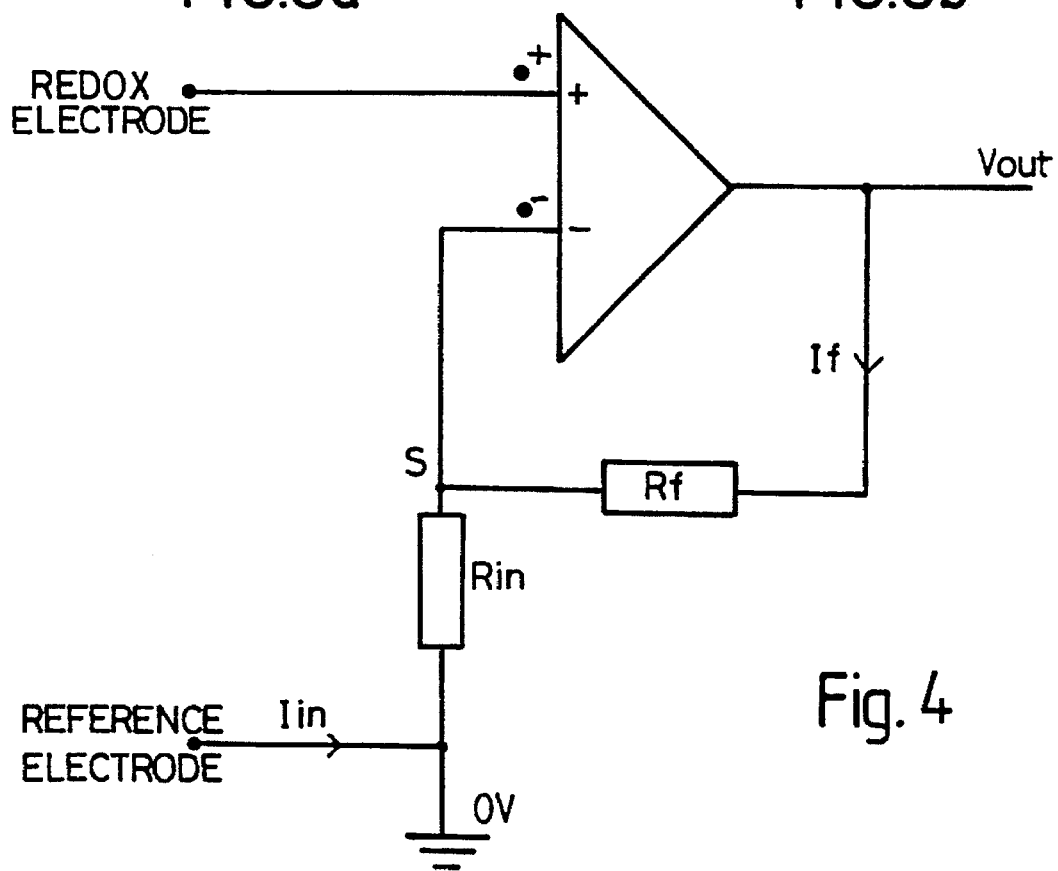
FIG. 4 is a measurement circuit for a potentiometric CFD.

For completeness, FIG. 3a shows a CFD designed for simple potentiometric measurement. The silver chloride reference electrode is referenced 24 and the carbon or gold redox working electrode 26. A layer of dielectric 20 bridges the electrodes. No guard electrode is shown. However, for practice of the present invention a guard electrode may be preferred, in which case the ceramic plate may carry an electrode formation similar to that of FIG. 1a. A potentiometric measurement circuit is shown in FIG. 4; this acts as a voltage follower to measure the total voltage change occurring at the working electrode over a given period of time.

The arrangements of FIGS. 1 to 4 are conventional except for the provision of the guard electrode, which constitutes an important second aspect of the present invention and will be referred to again later. Especially in the case of an electrode arrangement of the type shown in FIG. 1, a circular concentric electrode formation can be used instead of a rectangular one.

No reference has yet been made to the reagent layer 32 or 28 which is screen printed, in the case of the arrangements of both FIGS. 1 and 3, on the other (glass or polycarbonate) plate 30 of the CFD FIG. 1b and FIG. 3b. In the present invention, the reagent layer is a redox mediator incorporating an alkaline producing substance, e.g. an alkali metal hydroxide, in particular lithium hydroxide, although other alkali metal hydroxides or possibly more generally metal hydroxides could instead be employed. For practical purposes, the redox mediator is carried by a polymer solvent such as PVC, an acetate or cellulose, so as to constitute a screen printing ink. This can sometimes be deposited on the electrode plate instead of the opposing plate as shown, or be deposited in part on both plates. Plate 30 is superimposed over plate 10, as indicated by dashed lines 31 in FIGS. 1 and 3, at a spacing of about 0.2 mm.

The redox mediator is selected with respect to the reduction/oxidation reaction to be sensed in the CFD, also taking into account the reversibility of its redox couple, at the working electrode, in this case gold. In the present invention, therefore, the preferred redox mediator is a substance quickly soluble in the aqueous sugar-containing solution readily capable of being reduced by the reducing sugars in the solution, and readily reversed at the gold electrode. The selected redox mediator is therefore the ferricyanide ion, in the form of potassium ferricyanide.

The reagent layer is deposited over an area and thickness such that, when the sample liquid has been drawn by capillary action into the space between the plates, as large as possible amounts of ferricyanide and hydroxide ion are quickly taken into the system. Lithium hydroxide in excess can have a detrimental effect on ferricyanide solubility, and a preferred reagent layer therefore comprises 2.5M LiOH and 1M $K_3Fe(CN)_6$. Substantially reducing the amount of hydroxide ions detrimentally affects the reactivity of the system, and the quantitative balance between hydroxide and ferricyanide ions is therefore necessarily a compromise.

The importance of the guard electrode in the CFD will now be explained.

First, it has to be understood that, in the working coulometric CFD, for example using ferricyanide ions as the redox mediator for a sample containing a reducing sugar, the total current measurement results from the release of electrons at the working electrode when the ferrocyanide ions (having been reduced by the sugar) are re-oxidised.

The total current to be measured is that arising from the volume of sample liquid co-extensive with the working electrode. By the nature of a thin layer electrochemical measuring device such as a CFD, the reduction of ferricyanide ions to ferrocyanide ions and the consequential re-oxidation thereof is found to take place relatively quickly, so that after a relatively short period of time a plot of current versus time should evolve into a current plateau. However, if measurement is carried out using the coulometric measuring technique without a guard electrode, this plateau is not realized owing to sideways diffusion of reduced ions into the volume co-extensive with the working electrode from outside this volume. The required measurement can thus be falsified.

Figure 5:
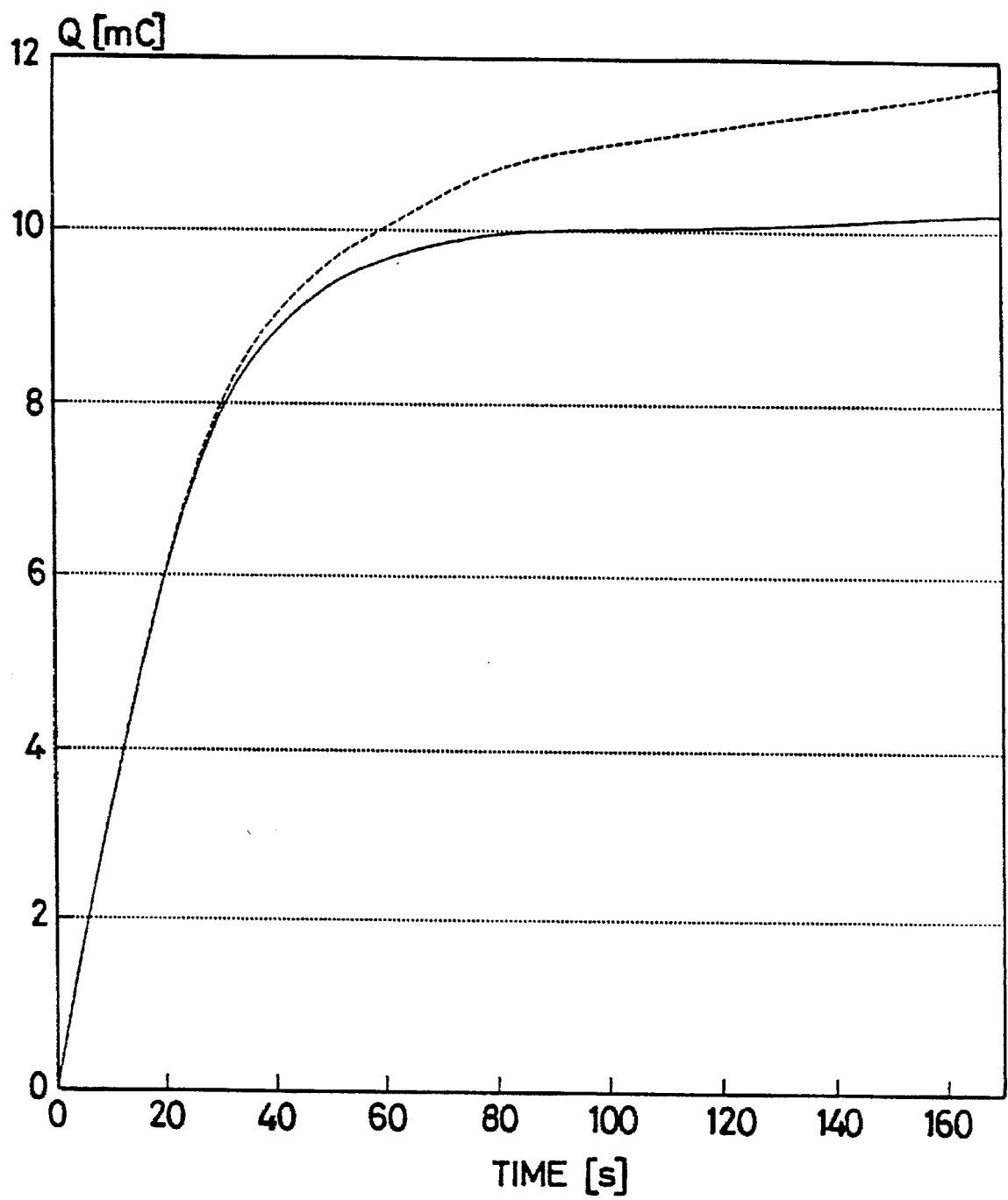
FIG. 5 is an explanatory graph of charge versus time relating to the use of a guard electrode in a CFD.

However, when a guard electrode is introduced, reduced ions diffusing into the said volume from outside are re-oxidized before reaching the working electrode, and the expected total current plateau is then realized in a current versus time graph. FIG. 5 shows the effect of introducing a guard electrode in a coulometric CFD, where the dotted curve indicates the sensor response without guard electrode and the solid line indicates the sensor response with guard electrode. The curves were obtained with a glucose sensor using 15 mM glucose solution, with reagents glucose oxidase, potassium ferricyanide, phosphate buffer at pH 7. A similar effect can be shown to arise with a potentiometric CFD.

It is easier for repetitive experimental testing to work with CFDs without the reagent layer than fully prepared CFDs, and numerous experiments have been carried out in this way, where necessary adding to the CFD both the ferricyanide ions and the hydroxide ions, as well as the sugar containing sample, by a pipette or the like. These experiments have tested the effects of varying the relevant parameters of the system, such as different concentrations of ferricyanide and hydroxide ions, different sources for the hydroxide ions, different sugars and different sugar concentrations, and different working voltages on the working electrode. Subsequently, prepared practical CFDs have been tested and the results obtained compared with the optimal results obtained during empty CFD testing. The significant results of these experiments are now briefly described.

Theoretically, the response, measured by the change in redox potential, should be governed by the Nernst Equation.

$$E = E° + RT/nF \, 1 \, n \, [Mox]/[Mred]$$

In this equation, E is the response potential, E° is the standard electrode potential (V), R is the Gas Constant 8.13 (kJ $mol^{-1}K^{-1}$), T is the temperature in Kelvin, n is the number of moles transferred per mole of species oxidised and F is the Faraday factor (-96500 C $mol^{-1}$), effectively constants, and [Mox] and [Mred] are the concentrations of the oxidised and reduced forms, respectively, of species M.

Consequently, the response of any device operating on this principle should be logarithmic. A sensor based on coulometric detection, for example should give a linear response.

Figure 6:
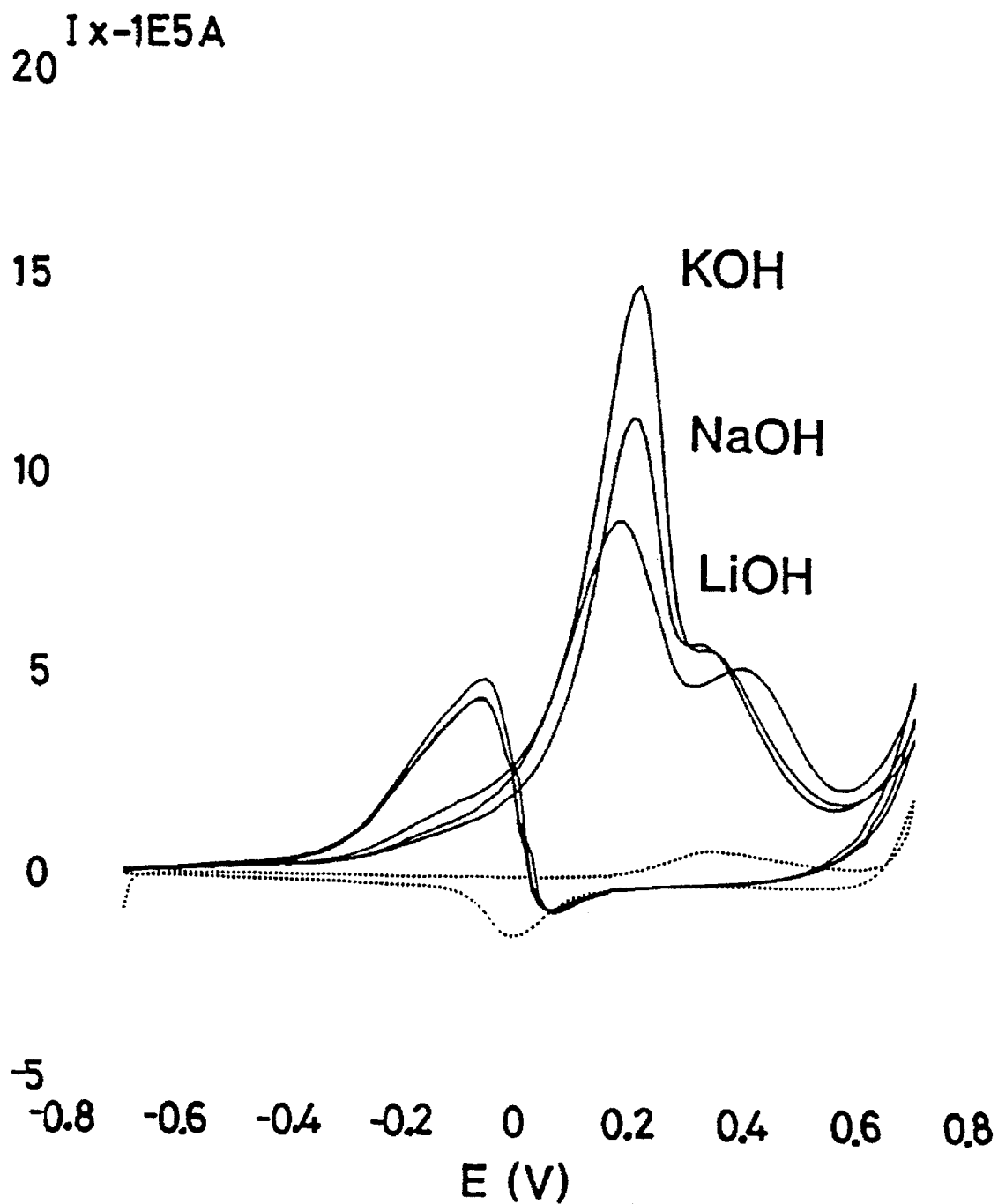
FIG. 6 is a voltametric response curve of current versus potential for fructose in a voltage scanned test CFD.

In practice, as a result of tests using cyclic voltametry in a CFD loaded with 400 mM fructose and 1M sodium hydroxide, it was shown that oxidation peaked with a working voltage on the gold working electrode in the range 200 to 300 millivolts. In fact, owing to the possible crystalline orientations of the gold electrode, twin peak activations were experienced in this range, but this is not significant. The same test was carried out with varying sodium hydroxide concentrations from 100 mM up to 5M, and likewise for potassium hydroxide and lithium hydroxide. The result of these experiments appeared to show that a preferred working voltage for the working electrode lies in the range 100 to 400 mV, preferably about 300 mV. When a guard electrode is used, the same voltage appeared appropriate for this electrode. FIG. 6 is representative of the voltametric response curves obtained for fructose in these experiments. The conditions were: 1M $NaNO_3$, v=100 mVs⁻¹, nitrogen saturated 400 mM fructose (reaction time 30 s). Potentials were scanned from −700 mV to 700 mV. The counter electrode was a gold disc, diameter 1.6 mm, with a Ag/AgCl reference electrode. The curves shown are for 1M LiOH, 1M NaOH and 1M KOH. Analogous results were obtained for other sugars.

Linear voltametry tests showed that the position and magnitude of the voltage peaks at the working electrode could vary to a limited extent with different fructose concentrations, possibly due to effects on the potential at the reference electrode, but these variations were not significant in the light of subsequent tests.

Thirdly, tests were carried out to attempt direct oxidation of fructose in the presence of sodium hydroxide at the working electrode, but no useful results were obtained.

Tests were then extended to experiments in which the redox mediator, ferricyanide ion, was also added to the empty CFD in combination with the sugar and the hydroxide ion.

Figure 7:
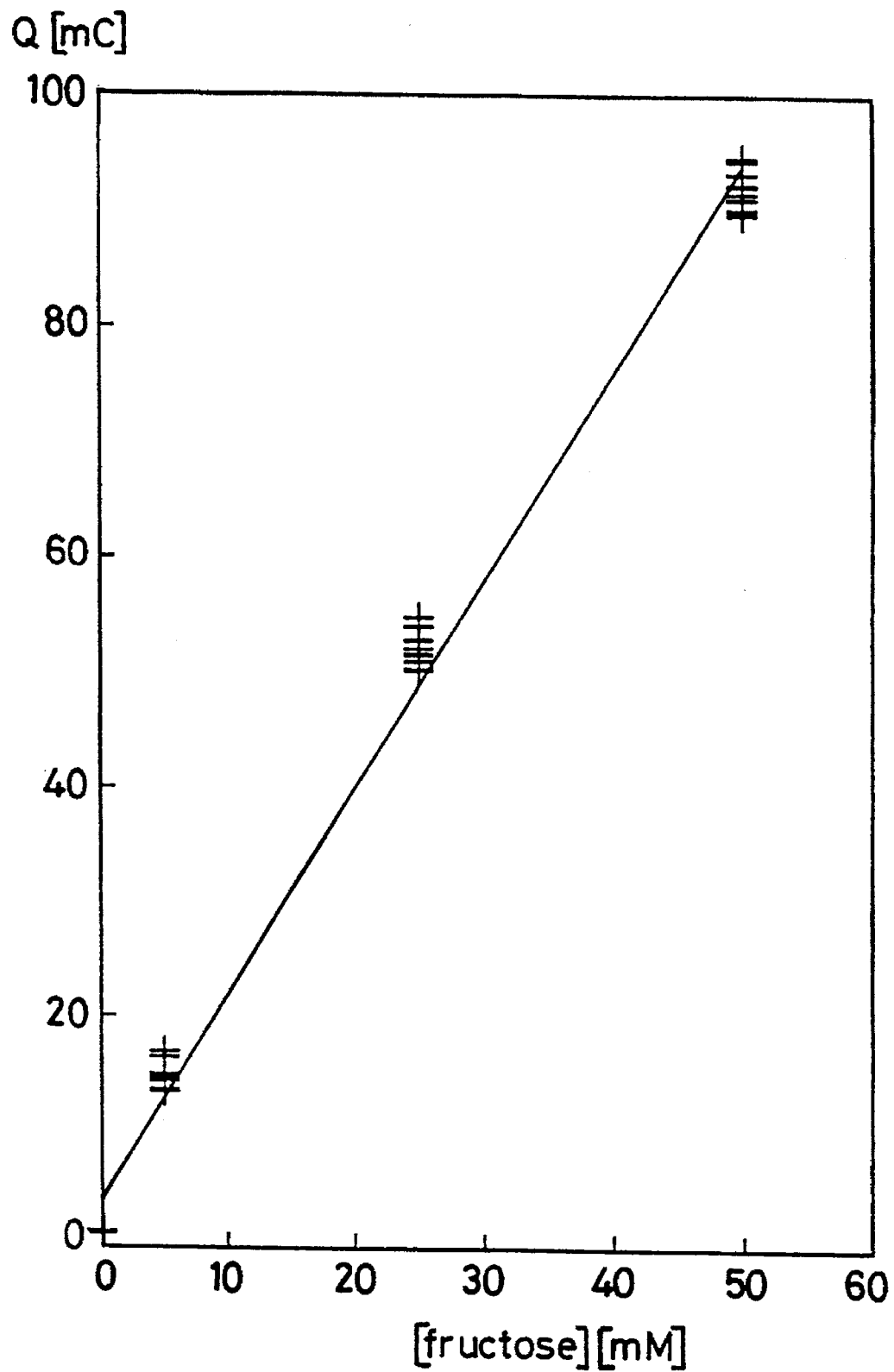
FIG. 7 is a fructose concentration versus total charge curve obtained in a test CFD (without redox couple)

Thus, it was shown that, as expected from theory, a linear response of total charge (in a coulometric CFD) with fructose concentration is obtained for the range 0 to 50 mM fructose concentration. The relevant graph of coulometric response is shown in FIG. 7. The conditions were 10 µl fructose solution+40 µl (1M $K_3Fe(CN)_6$, 2.5M LiOH, reaction time 60 s, potential 300 mV.

A second series of experiments reinforced previous results that a preferred voltage range for the working electrode is 100 to 400 mV.

Figure 8:
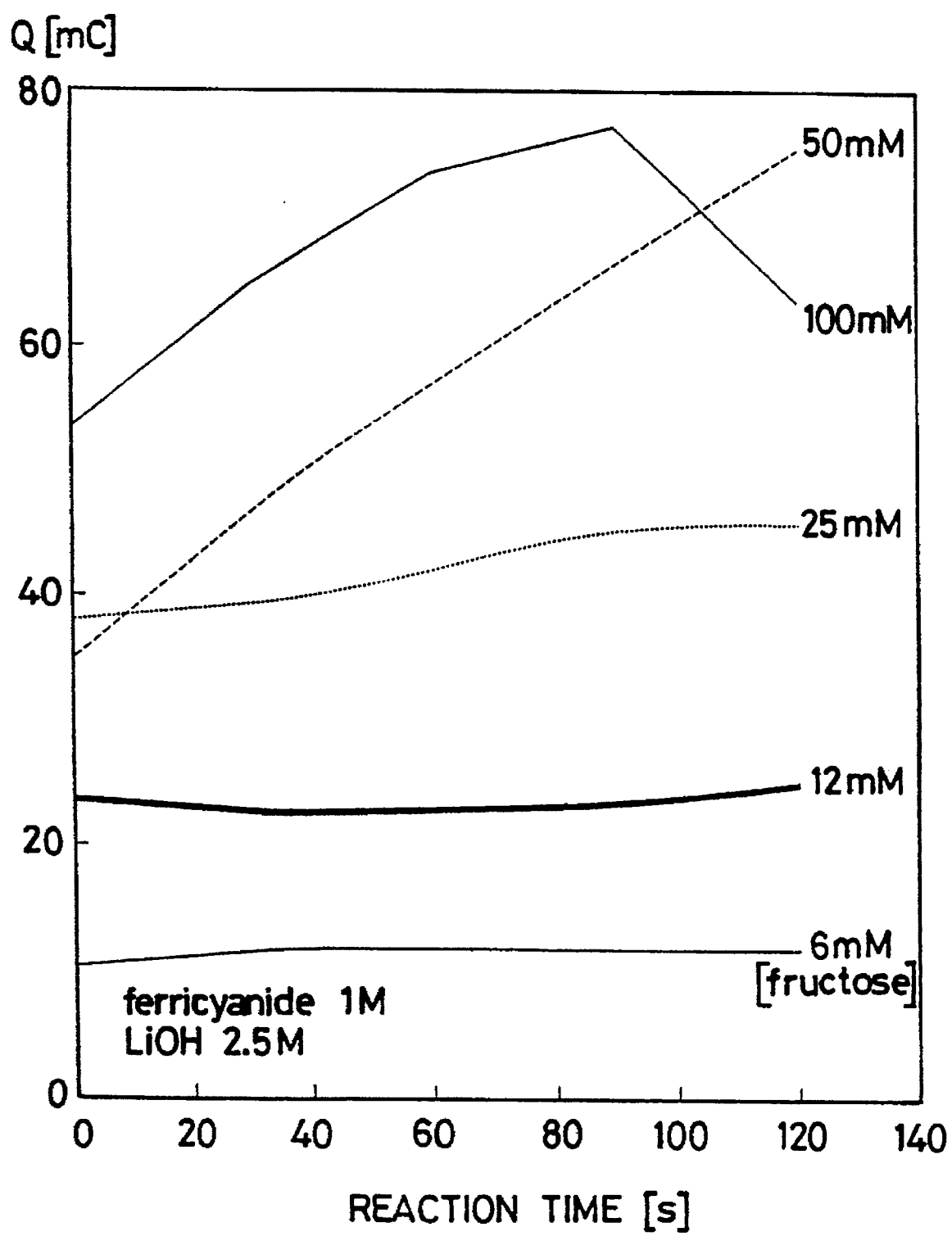
FIG. 8 is a total charge versus time graph obtained for varying fructose concentrations in a test CFD loaded with a redox mediator.

A third series of experiments then tested the effects of variation of the fructose concentration in a CFD, also loaded with ferricyanide and hydroxide ions, on the total measured charge. The graphs of FIG. 8 show coulometric response for fructose in empty CFDs: effect of reaction time. The conditions were 10 µl fructose solution plus 40 µl (2.5M LiOH/1M $K_3Fe(CN)_6$). The working potential was 300 mV. Ideally, the curves should be substantially flat, but the results show that, above a fructose concentration of about 50 mM, a number of effects take place which influence the total measured charge. Above a concentration of 100 mM, a reduction in the measured total charge can occur. It is not necessary to go into the reasons for the effects which take place, but absorption of fructose at the silver reference electrode and a consequential shift in potential at the reference electrode are believed to be of some significance.

More importantly, the curves of FIG. 8 demonstrate the potential usefulness of the method of the invention using a CFD sensor. Very high, easily measurable, total charge levels are experienced, much larger than in beaker chemistry but at room temperature, in very short times not exceeding two minutes. For measuring sugar levels in the range 0 to 25 mM particularly, but possibly up to 50 mM, which is the range experienced in many biological liquids, including silage liquors, the method appears highly practical.

Further, practical CFDs generally in accordance with FIG. 1, provided with reagent layers of ferricyanide and hydroxide ions have been tested by making electrochemical measurements on a series of calibration and test sugar solutions. These are now briefly discussed.

Stock solutions of the sugars glucose, fructose and galactose were prepared by diluting 9 g of the sugar in 100 ml water. Aliquots of the stock solution were taken to prepare the calibration solutions of concentrations 1.5, 3.12, 6.25, 12.5, 25 and 50 mmol/l by dilution into the appropriate volume of water.

20 microlitres of the sugar solution was inserted into a fresh CFD, the inner surface of which carried a reagent layer comprising 33 per cent lithium hydroxide and 67 per cent ferricyanide in a PVC matrix, and which resulted (after dilution with the aqueous sample applied) in a solution which was saturated with respect to ferricyanide (i.e. a concentration of about 1 molar), and about 3–5 molar with respect to lithium hydroxide.

Figure 10:
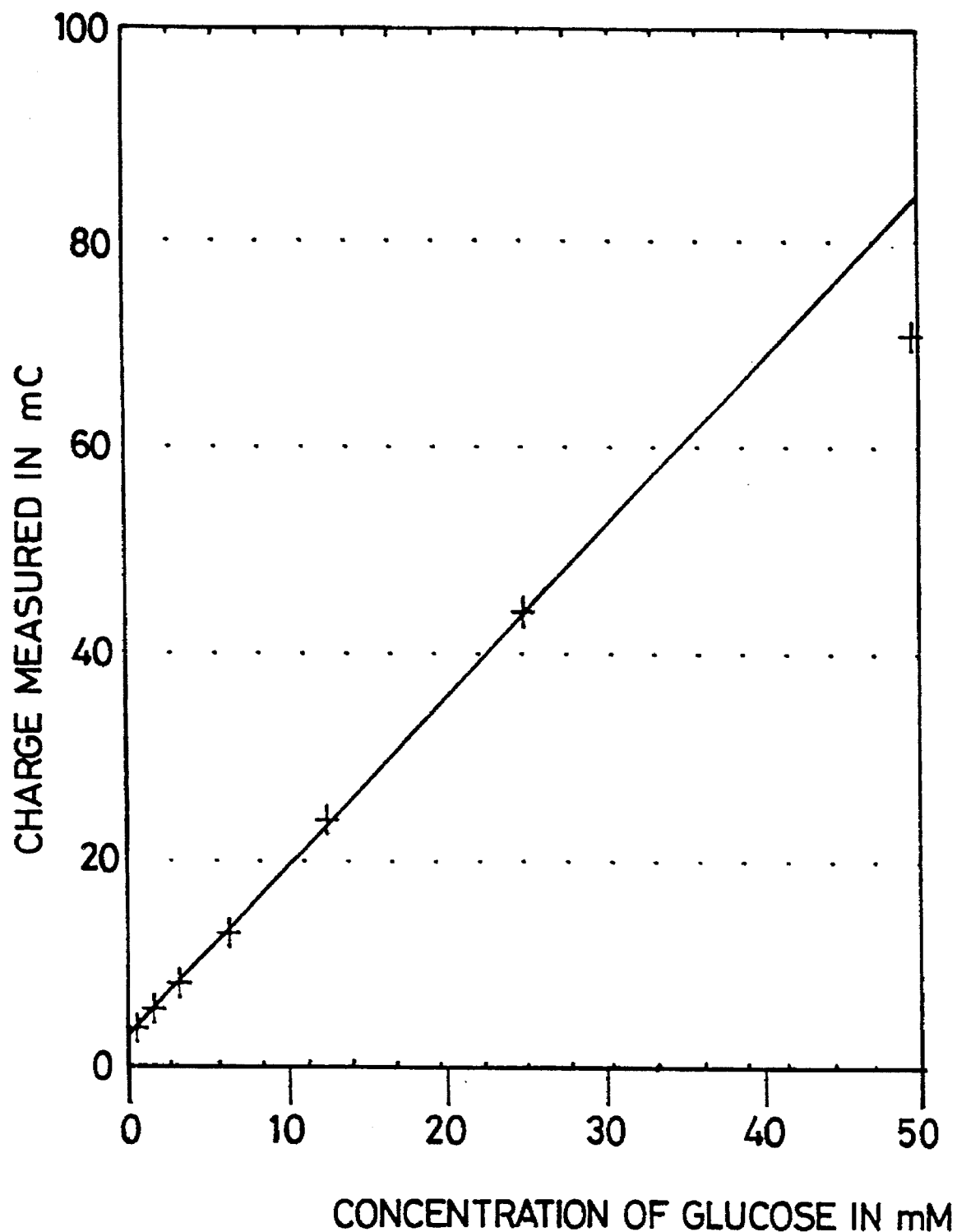
Figure 11:
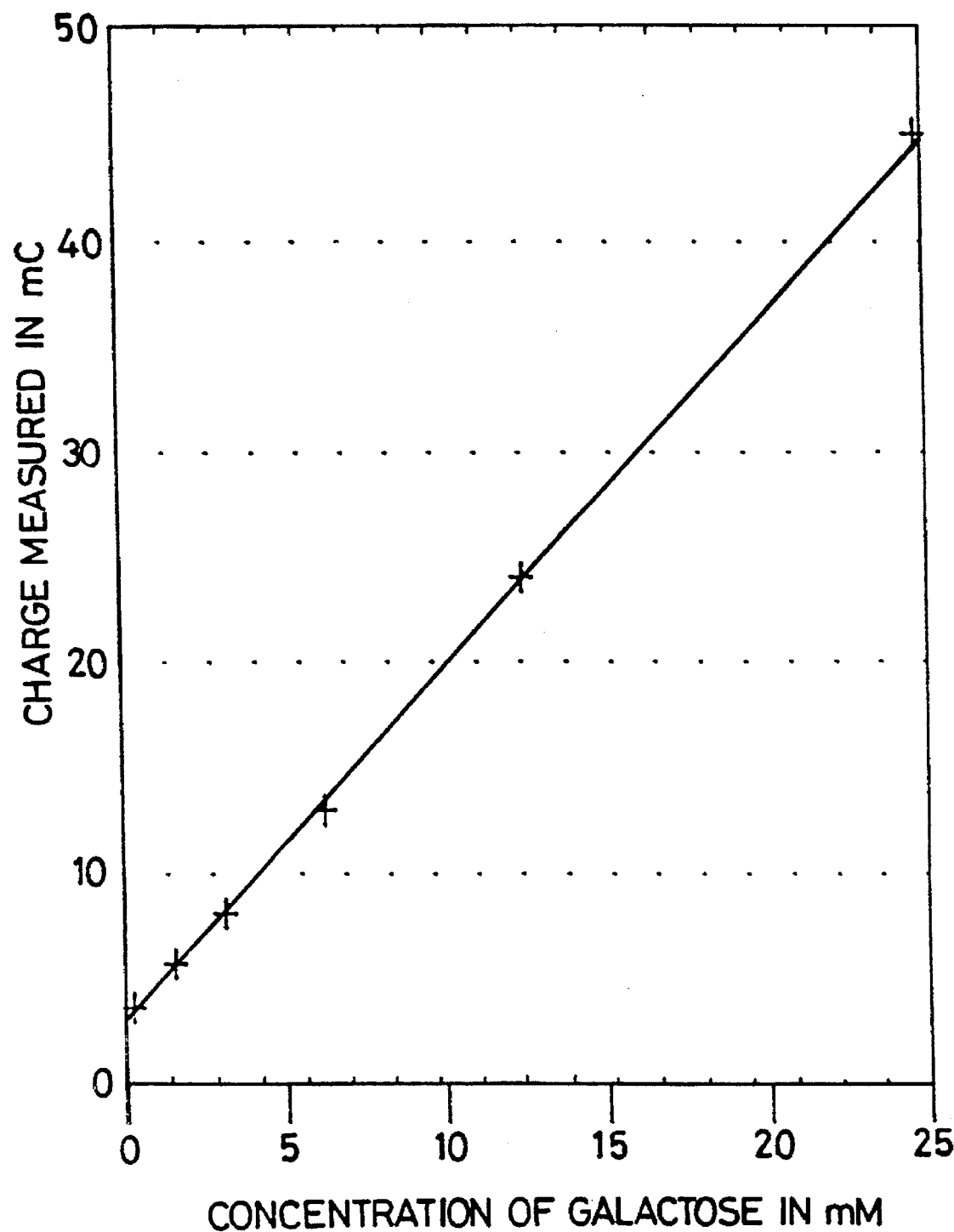

The solution was allowed to equilibrate in the CFD for approximately one minute. The concentration of ferrocyanide was then measured by controlled potential coulometry using a M270 EG&G potentiostat. The results were as shown in Table 1, and represented graphically in FIGS. 9–11.

Figure 9:
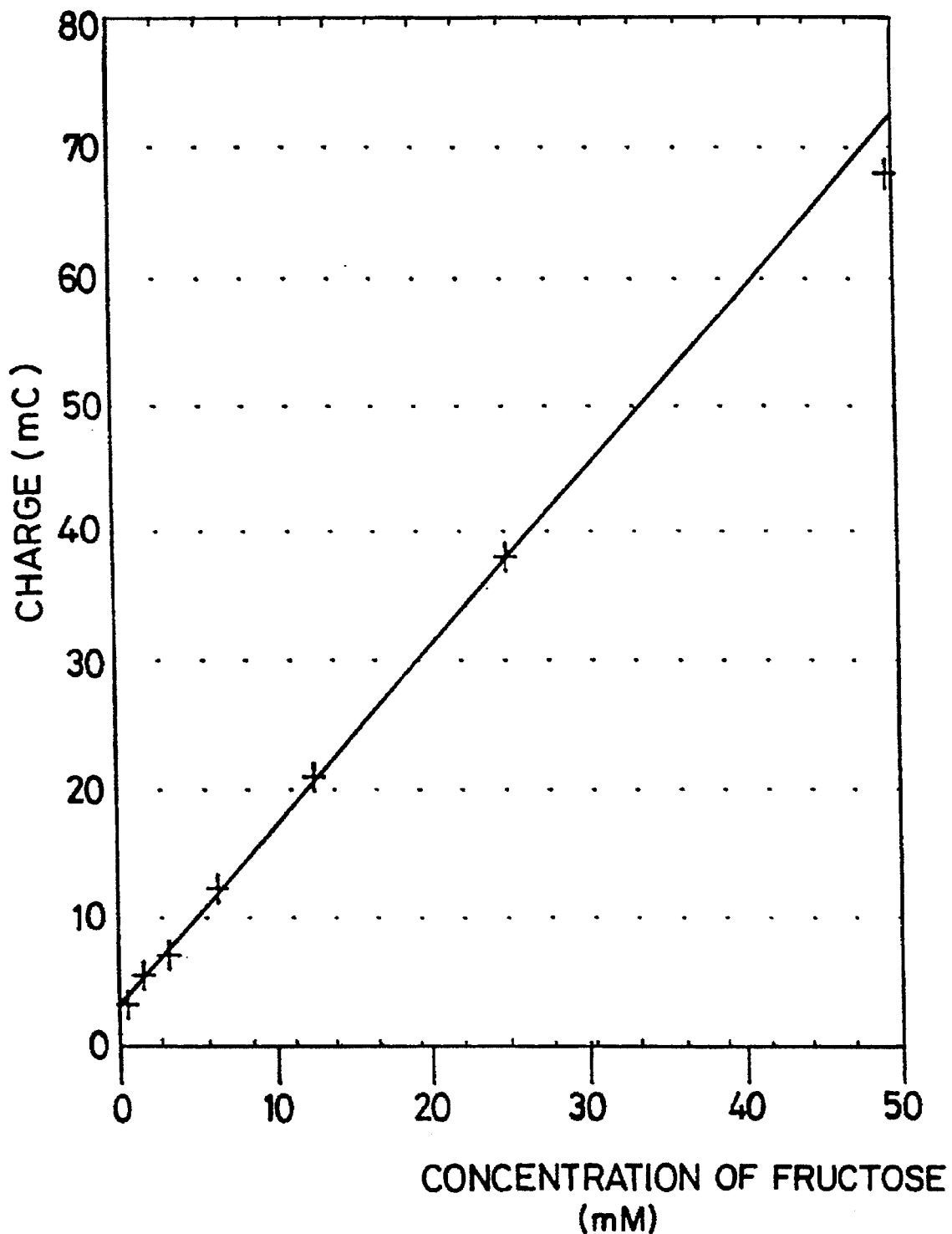
FIGS. 9 to 11 are graphs of charge versus concentration showing measurement results obtained with a practical CFD for different sugars: fructose (FIG. 9), glucose (FIG. 10) and galactose (FIG. 11)

For FIG. 9, charge=1.30. conc+3.83. Corr=99.8.
For FIG. 10, charge=1.63. conc+3.13. Corr=99.9.
For FIG. 11, charge=1.67. conc+3.07. Corr=99.9.

TABLE 1

| Concentration of sugar solution | Charge measured in mC | | |
|---|---|---|---|
| (mmol/l) | Fructose | Glucose | Galactose |
| 50 | 68 | 71 | 57 |
| 25 | 38 | 44 | 45 |
| 12.5 | 21 | 24 | 24 |
| 6.25 | 12 | 13 | 13 |
| 3.12 | 7 | 8 | 8 |
| 1.5 | 5 | 5 | 5 |
| 0 | 3 | 3 | 3 |

Following calibration, aliquots of silage liquor samples of known total reducing sugars concentrations (determined by conventional techniques) were analyzed in identical CFDs to those in which the calibration experiments were carried out by the same experimental protocol as described above. The results are shown in Table 2, and graphically in FIG. 12. For FIG. 12, charge=1.78. conc+17.65. Corr=95%.

TABLE 2

| Concentration of total reducing sugars (mmol/l) | Charge measured (mC) |
|---|---|
| 1 | 19 |
| 5 | 23.5 |
| 7 | 36 |
| 12 | 38 |
| 24 | 55 |
| 28 | 72 |

Figure 12:
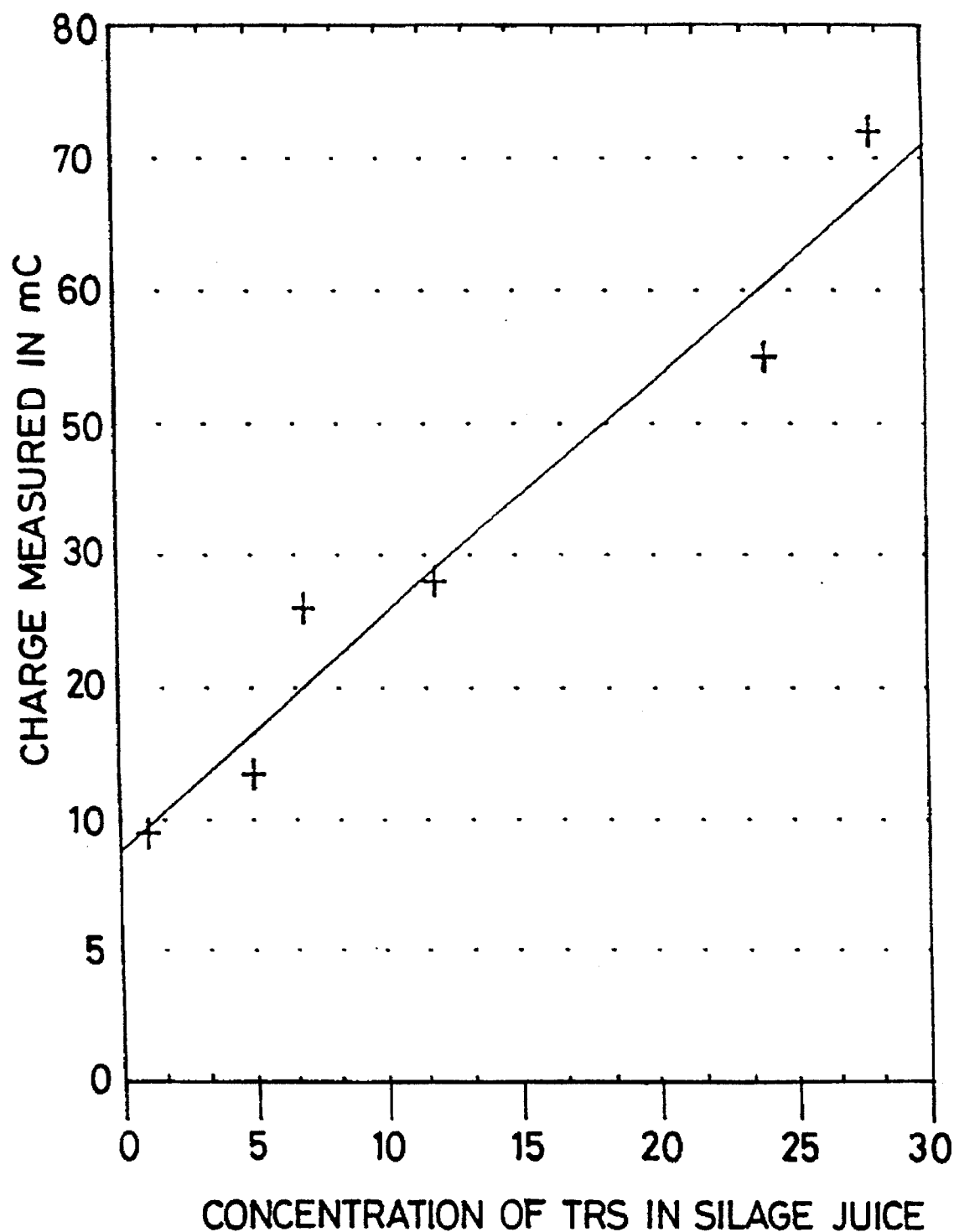
FIG. 12 is a graph of charge versus sugar concentration, showing results obtained in a practical CFD with silage liquor.

The results of Table 2 and FIG. 12, especially, show that the method of the invention employing a CFD is able quantitatively to assess the reducing sugar content of an aqueous liquid containing a mixture of sugars with acceptable accuracy.

Figure 13:
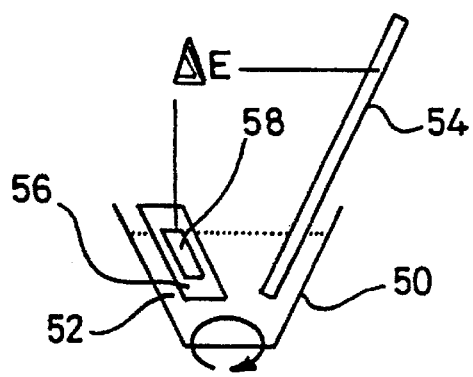
FIG. 13 is a schematic diagram of a forced convection cell.

Further experimental work has been carried out using a forced convection cell (FCC), as shown in FIG. 13, which is an accepted laboratory equivalent of a CFD.

The cell comprises a vessel 50 for receiving test solution 52 into which dip a silver/silver chloride double junction reference electrode 54 and a plate 56 bearing a printed gold electrode 58. Forced mixing of the solution is effected, and ΔE measured between the electrodes.

This further work was performed using a potentiometric measurement circuit instead of a coulometric measurement circuit. In practice, data was captured with a Keithley electrometer interfaced to lotus measure via a GPIB card.

Figure 14:
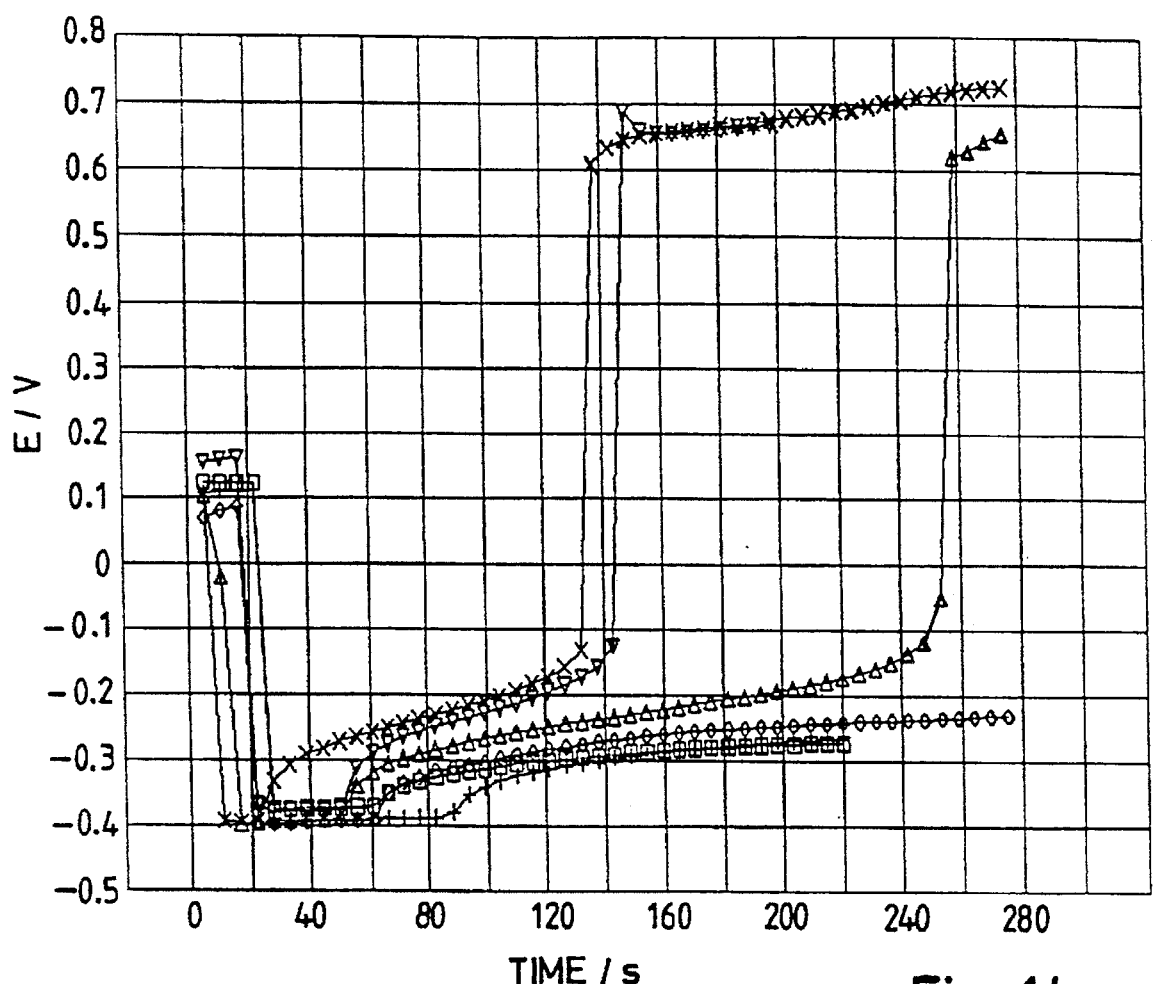
FIGS. 14 to 16 are curves showing various test results obtained using a forced convection cell.
Figure 15:
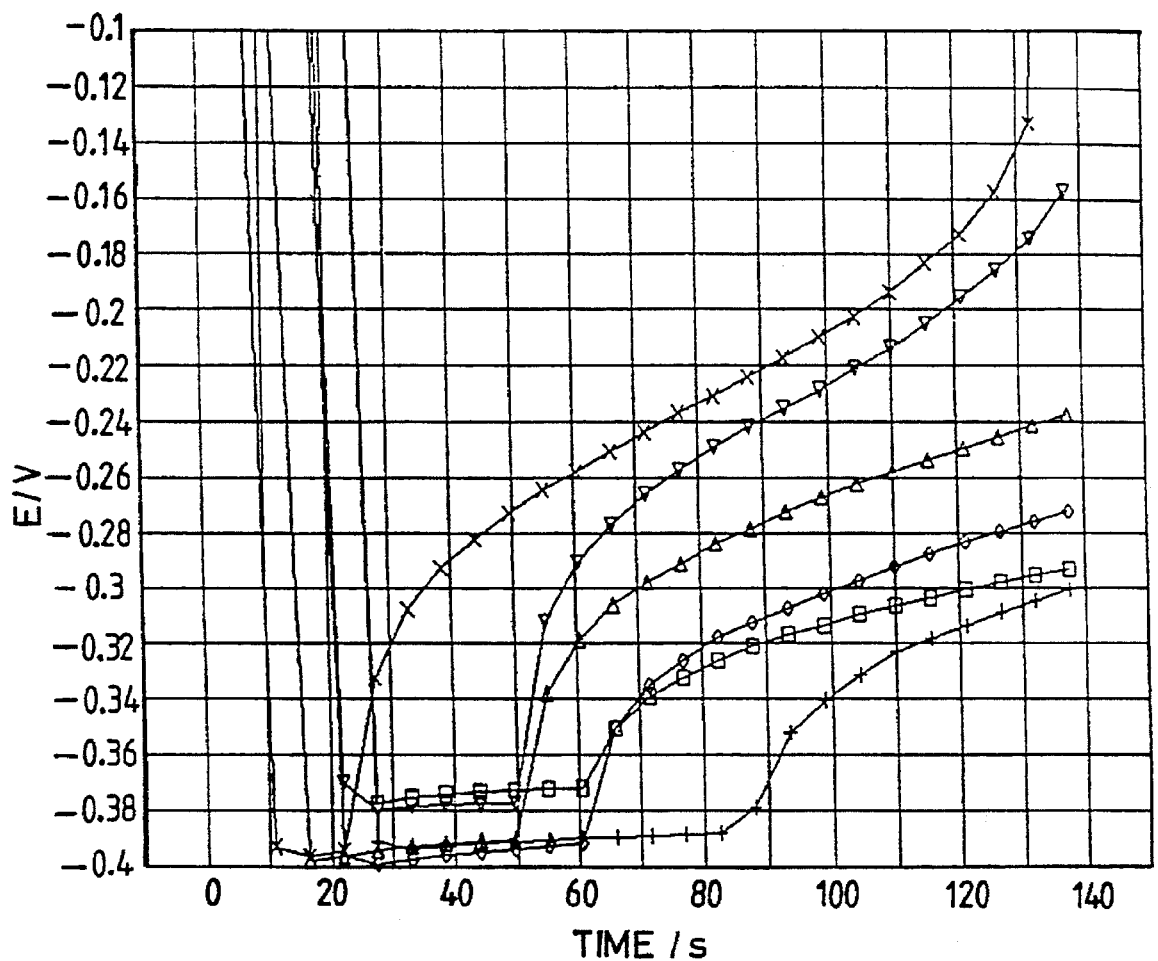
Figure 16:
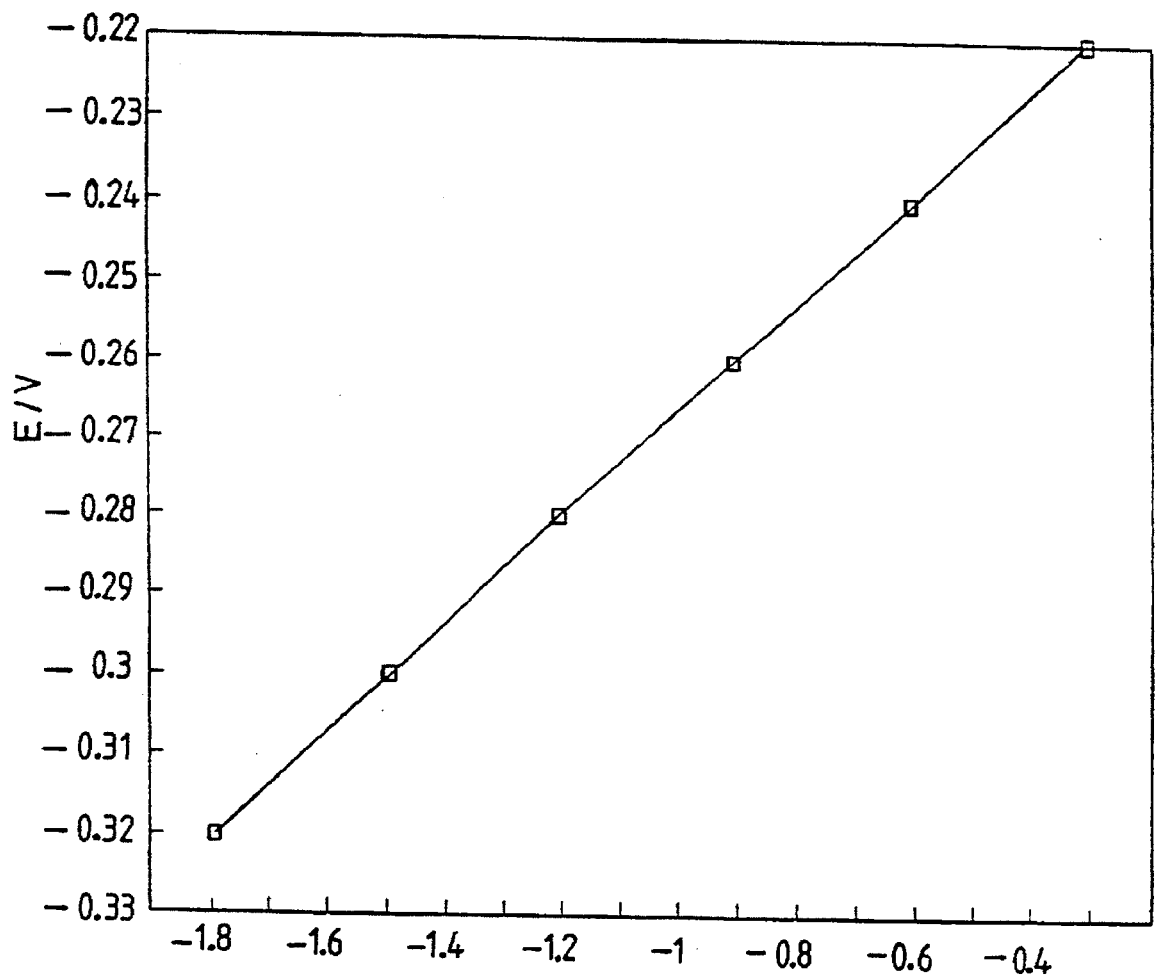

FIGS. 14, 15 and 16 show the potentiometric response to the addition of solutions containing fructose to a mixture containing ferricyanide and lithium hydroxide (at working volumes 0.25M and 2M respectively) using the FCC of FIG. 13. In FIGS. 14 and 15 curves are given for different concentrations of fructose as follows:

☐ 0.016M
+ 0.031M
◊ 0.062M
∆ 0.125M
× 0.25M
▽ 0.5M

FIG. 15 shows part of the curves of FIG. 14 to an enlarged scale. On addition of ferricyanide to solutions containing lithium hydroxide the electric polarisation of the system is rapidly reversed, appearing negative in FIG. 14. As shown in these Figures, addition of solutions containing fructose initiate a reversal of the potential (becoming more positive). At concentrations of fructose greater than 0.125M the original electric polarisation is attained; the potential becomes positive for all concentrations of fructose greater than 0.125M. At the point of transition between negative and positive potentials the colour of the solution undergoes a change from yellow (the colour of solutions containing ferricyanide the oxidised form), to clear (the colour of solutions of ferrocyanide the reduced form). This behaviour is evidence for the (approximate) stoichiometric oxidation of fructose by ferricyanide. The equation describing the reduction of ferricyanide is well known, equation:

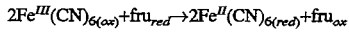

$$2Fe^{III}(CN)_{6(ox)} + fru_{red} \rightarrow 2Fe^{II}(CN)_{6(red)} + fru_{ox}$$

The realisation that two moles of ferricyanide are required for the oxidation of one mole of fructose is supported by the fact that the same stoichiometric relationship exists for the oxidation of glucose, another hexose sugar, by ferricyanide.

Ferricyanide has to be employed at a concentration of 1M in order to completely oxidise the fructose present at the maximum concentration, 0.5M. This is at the limit of the solubility of ferricyanide. However, although it was not practical to use 1M ferricyanide in the tests because of the requirement to keep the solution components separate, there is support for the use of 1M ferricyanide in a CFD.

By utilising dried printed layers of salts including ferricyanide, a concentration of ferricyanide of 1M was routinely achieved in a glucose CFD, originally developed for blood glucose monitoring for use by insulin dependent diabetics.

In spite of the aforesaid limitations it is possible to demonstrate a relationship between potential response and concentration of fructose which is in accordance with the Nernst equation. FIG. 16 shows the potential response v.log ([fructose]) for each of the tests illustrated in FIGS. 14 and 15. The potential was taken before the reversal of polarisation of the electrodes, in each case 50 seconds after the addition of fructose. The slope of FIG. 16 is about 0.067 E/log.M.

A final point which has emerged from tests using KOH, NaOH and LiOH, especially the last two, is that lithium hydroxide, although less active than sodium hydroxide, is less hygroscopic, and in practical use of a total sugar sensor, for example for measuring sugar content of silage on site, lithium hydroxide would present less problems of storage, although storage under sealed conditions with a desiccant would remain essential. Generation of an alkaline environment in situ within the device, e.g. using the technique disclosed in WO94/15207, has the advantage of overcoming storage problems due to instability of alkaline salts.

We claim:

1. A non-enzymic method of selectively determining the content of reducing sugars only in an aqueous solution, comprising forming a thin layer having a thickness of less than about 1 mm of a solution to be tested in an alkaline environment containing a soluble redox mediator and in the absence of enzymes catalyzing reactions of reducing sugars;

determining electrochemically the amount of reduction product of the redox mediator; and determining from the amount of reduction product the content of reducing sugars in the aqueous solution.

2. A method according to claim 1, wherein the redox mediator comprises ferricyanide.

3. A method according to claim 1, wherein the mediator is present in an amount to form a saturated solution.

4. A method according to claim 1, wherein the thin layer has a thickness of less than about 0.5 mm.

5. A method according to claim 4, wherein the thin layer has a thickness of less than about 0.2 mm.

6. A method according to claim 1, wherein the alkaline environment is formed by a soluble alkaline producing substance.

7. A method according to claim 6, wherein the soluble alkaline producing substance comprises an alkali metal hydroxide.

8. A method according to claim 7, wherein the alkali metal hydroxide comprises sodium hydroxide or lithium hydroxide.

9. A method according to claim 7, wherein the hydroxide is present at a concentration of at least about 1 molar.

10. A method according to claim 9, wherein the hydroxide is present at a concentration of not greater than about 5 molar.

11. A method according to claim 1, wherein the aqueous solution comprises a sample of silage liquor.

12. A method according to claim 1, wherein the reducing sugars content in the solution is not more than about 50 mM.

13. A method according to claim 12, wherein the reducing sugars content in the solution is in the range 0 to 25 mM.

14. A method according to claim 1, carried out in a thin layer electrochemical measurement device, an inner surface of which has a coating of at least one soluble redox mediator, the device including means for producing an alkaline environment.

15. A method according to claim 14, wherein the soluble redox mediator includes a soluble alkaline producing substance.

16. A method according to claim 15, wherein the soluble alkaline producing substance comprises an alkali metal hydroxide.

17. The method according to claim 1, wherein the concentration of hydroxyl ions is adjusted depending on the approximate expected sugar concentration range of the solution being tested.

* * * * *